United States Patent
Karpenkop et al.

(10) Patent No.: US 11,589,775 B2
(45) Date of Patent: Feb. 28, 2023

(54) ALARM LIMITS UPDATE SYSTEM FOR A MEDICAL MONITORING DEVICE

(71) Applicant: ORIDION MEDICAL 1987 LTD., Jerusalem (IL)

(72) Inventors: Ido Karpenkop, Yavne (IL); Robert Istrate, Landgraaf (NL); Michal Ronen, Jerusalem (IL); Yossef Hay Cohen, Jerusalem (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 906 days.

(21) Appl. No.: 16/123,035

(22) Filed: Sep. 6, 2018

(65) Prior Publication Data
US 2019/0076055 A1    Mar. 14, 2019

Related U.S. Application Data

(60) Provisional application No. 62/558,129, filed on Sep. 13, 2017.

(51) Int. Cl.
| | | |
|---|---|---|
| *A61B 5/083* | (2006.01) | |
| *G08B 21/02* | (2006.01) | |
| *G16H 50/20* | (2018.01) | |
| *A61B 5/00* | (2006.01) | |

(52) U.S. Cl.
CPC ............ *A61B 5/0836* (2013.01); *A61B 5/746* (2013.01); *G08B 21/02* (2013.01); *G16H 50/20* (2018.01); *A61B 2560/0252* (2013.01); *A61B 2560/0257* (2013.01)

(58) Field of Classification Search
CPC .................. A61B 5/0836; A61B 5/746; A61B 2560/0257; A61B 2560/0252; G16H 50/20; G08B 21/02
See application file for complete search history.

(56) References Cited

U.S. PATENT DOCUMENTS

| | | | |
|---|---|---|---|
| 9,877,671 B2 * | 1/2018 | Chang | .................. A61B 5/6843 |
| 2015/0112171 A1 | 4/2015 | Chang | |
| 2015/0316520 A1 | 11/2015 | Maguire et al. | |
| 2017/0000424 A1 | 1/2017 | Friedman et al. | |

OTHER PUBLICATIONS

International Search Report and Written Opinion for PCT Application No. PCTIL2018/050993 dated Dec. 10, 2019; 11 pgs.

* cited by examiner

*Primary Examiner* — Navin Natnithithadha
(74) *Attorney, Agent, or Firm* — Cantor Colburn LLP

(57) ABSTRACT

Disclosed herein are devices, systems, and methods for updating alarm limits applied in monitoring one or more medical parameters of a subject. The devices, systems, and methods obtain a measurement of ambient pressure at a defined time point ('$t_1$') and compare the measurement of ambient pressure at the defined time point ('$t_1$') to a reference ambient pressure. If a difference between the measured ambient pressure values at $t_1$ and the reference ambient pressure is at or above a predetermined threshold, the alarm limits are updated to correspond with the ambient pressure at $t_1$ or a user is alerted to update the alarm limits.

20 Claims, 3 Drawing Sheets

ALARM LIMITS UPDATE SYSTEM FOR A MEDICAL MONITORING DEVICE

CROSS-REFERENCE TO RELATED APPLICATION

This application claims priority to and the benefit of U.S. Provisional Application Ser. No. 62/558,129, entitled "ALARM LIMITS UPDATE SYSTEM FOR A MEDICAL MONITORING DEVICE," filed Sep. 13, 2017, the content of which is incorporated herein by reference in its entirety for all purposes.

TECHNICAL FIELD

The present disclosure generally relates to the field of medical device alarms.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Medical monitoring devices provide crucial data regarding a patient's medical condition. For example, capnographs measure and provide carbon dioxide ($CO_2$) related parameters in exhaled breath and, as such, may be used to characterize a patient's condition and particularly ventilation functionality.

Medical devices may trigger an alarm, alerting health care providers that a monitored parameter deviates from a threshold value. For example, a capnograph may activate an alarm when deviations or changes in the patient's $CO_2$ levels are detected.

SUMMARY

Aspects of the present disclosure relate to devices, systems, and methods for providing alarm limits updates based on an ambient pressure. The devices, systems, and methods may automatically detect when a change and/or a rate of change of ambient pressure reaches or exceeds a predetermined threshold (e.g., due to changes in altitude), and updates the alarm limits. The alarm limits may be updated either automatically or by alerting a user/caregiver to consider updating the alarm limits due, in part, to the change in ambient pressure.

Current $CO_2$ monitoring devices, such as capnographs, may be set to define $CO_2$ alarm limits, such that a deviation in a $CO_2$ related parameter value (for example, $CO_2$ concentration or any other monitored parameter) below or above a predefined threshold may be indicative of deterioration in a subject's medical condition. Generally, measured $CO_2$ related parameters may vary with ambient pressure at the patient's treatment location. In certain clinical settings, the patient may be transferred from one location to another location. The ambient pressure may vary from one location to another. Therefore, due, in part, to the change in ambient pressure from one location to another, previously set alarm limits that are suitable at one location may no longer be suitable for the new patient at another location. As such, false alarms may be activated and interfere with the patient's treatment.

The term "threshold," in accordance with some embodiments, may refer to a value or a range of values. The thresholds disclosed herein may be preset at manufacturing, or may be preset by an operator (e.g., medical professional), for example.

In an exemplary case, in which the patient is air lifted (e.g., by a helicopter), ambient pressure may decrease due to altitude elevation. Consequently, $CO_2$ readings may drop below a minimum (e.g., lower) alarm threshold and falsely activate the alarm. The disclosed devices, systems, and methods may be used to update the alarm limits when the patient is moved from one location to another (e.g., from a low elevation location to a higher elevation location) to comply with a detected ambient pressure, and thereby reduce the chance of false alarms.

According to some embodiments, a method for updating alarm limits applied in monitoring one or more medical parameters of a patient is provided. The method includes measuring ambient pressure at a defined time point ('$t_1$'); comparing the ambient pressure measured at the defined time point ('$t_1$') to a reference ambient pressure; and if a difference between the measured ambient pressure at $t_1$ and the reference ambient pressure is at or above a predetermined threshold, updating the alarm limits to comply with the ambient pressure at $t_1$ or alerting a user to update the alarm limits. Optionally, the reference ambient pressure may be measured at a first time point ('$t_0$'), for example, before the subject is transferred to a different location/altitude. Alternatively, the reference ambient pressure may be a predetermined value.

According to some embodiments, a method for updating alarm limits applied in monitoring one or more medical parameters of a subject is provided. The method includes measuring ambient pressure at a defined time point ('$t_1$'); comparing the ambient pressure measured at the defined time point ('$t_1$') to a reference ambient pressure measured at a first time point ('$t_0$'); if a difference between the measured ambient pressure at $t_1$ and the reference ambient pressure at $t_0$ is at or above a predetermined threshold, comparing a measured/computed altitude at $t_1$ to a reference altitude (e.g., measured, computed, or predetermined) at $t_0$; and if the measured altitude deviates from the reference altitude, updating the alarm limits to comply with the ambient pressure at $t_1$ or alerting a user to update the alarm limits.

According to some embodiments, a method for updating alarm limits applied in monitoring one or more medical parameters of a subject, is provided. The method includes measuring a rate of ambient pressure change; comparing the rate of change to a predefined threshold; and if the rate of change of ambient pressure is at or above the predefined threshold, updating the alarm limits or alerting a user to update the alarm limits.

According to some embodiments, a method for updating alarm limits during monitoring of one or more medical parameters is provided. The method includes measuring a rate of ambient pressure change; comparing the rate of change to a predefined threshold; if the rate of ambient pressure change is above the predefined threshold, comparing a measured/computed altitude to a reference altitude; and if the measured altitude deviates from the reference altitude (e.g., initial altitude), updating the alarm limits or alerting a user to consider updating the alarm limits.

According to some embodiments, there is provided an alarm limits updating system having a control logic that may receive a measured rate of change of ambient pressure; compare the measured rate of change to a predetermined threshold value; and if the rate of change of ambient pressure is at or above the predefined threshold, updating the alarm limits or alerting a user to update the alarm limits. Optionally, the control logic may also compare a measured altitude to a reference altitude when the measured pressure rate is at or above the threshold value; and update alarm limits or alerting that such an update may be needed when the measured altitude deviates from the reference altitude.

According to some embodiments, there is provided herein a method for updating alarm limits applied in monitoring one or more medical parameters of a subject, the method including the steps of: obtaining a measurement of ambient pressure at a defined time point ('$t_1$'); comparing the measurement of ambient pressure to a reference ambient pressure; in case a difference between the measured ambient pressure at $t_1$ and the reference ambient pressure is at or above a predetermined threshold, updating the alarm limits to comply with the ambient pressure at $t_1$ or alerting a user to consider updating the alarm limits. The alarm limits may be applied in monitoring one or more medical parameters of a subject and the one or more medical parameters may be affected by a change in ambient pressure. According to some embodiments, the method may further include the step of measuring the ambient pressure at the defined time point ('$t_1$'). The reference ambient pressure may be measured at a first time point ('$t_0$'). The reference ambient pressure may be a predetermined value.

According to some embodiments, there is provided herein a method for updating alarm limits applied in monitoring one or more medical parameters of a subject, the method including the steps of: obtaining a measurement of a rate of change of ambient pressure during the monitoring of the one or more medical parameters; comparing the rate of change of ambient pressure to a predefined threshold; if the rate of change of ambient pressure is at or above the predefined threshold, updating the alarm limits or alerting a user to update the alarm limits. The method may further include the step of measuring the rate of change of ambient pressure.

According to some embodiments, there is provided a device for updating alarm limits applied in monitoring one or more medical parameters of a patient, the device comprising a control logic that may receive a signal indicative of a change and/or rate of change of ambient pressure, compare the change and/or rate of change to a predetermined threshold value, and if the change and/or rate of change of ambient pressure is at or above the predefined threshold, update the alarm limits or alert a user to update the alarm limits. The alarm limits are applied in monitoring one or more medical parameters of a patient and the one or more medical parameters are affected by a change in ambient pressure.

According to some embodiments, there is provided a system for updating alarm limits applied in monitoring one or more medical parameters of a patient, the system including a control logic that may receive a signal indicative of change and/or rate of change of ambient pressure, compare the change and/or rate of change to a predetermined threshold value, and if the change and/or rate of change of ambient pressure is at or above the predefined threshold, update the alarm limits or alert a user to update the alarm limits. The alarm limits are applied in monitoring one or more medical parameters of a patient; and a sensor may measure the one or more medical parameters. The one or more medical parameters may be affected by a change in ambient pressure. The system may further include a pressure sensor that may measure ambient pressure values and communicate the measured values to the control logic.

According to some embodiments, the one or more medical parameters may include a $CO_2$ related parameter. The $CO_2$ related parameter may be selected from the group consisting of: $EtCO_2$, $CO_2$ waveform and parameters related thereto, respiration rate, breath cycle, $CO_2$ concentration in expired air, and any combination thereof. The $CO_2$ related parameter may include $EtCO_2$.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced. The figures are for the purpose of illustrative discussion and no attempt is made to show structural details of an embodiment in more detail than is necessary for a fundamental understanding of the teachings of the disclosure. For the sake of clarity, some objects depicted in the figures are not to scale.

DETAILED DESCRIPTION

Figure 1A:
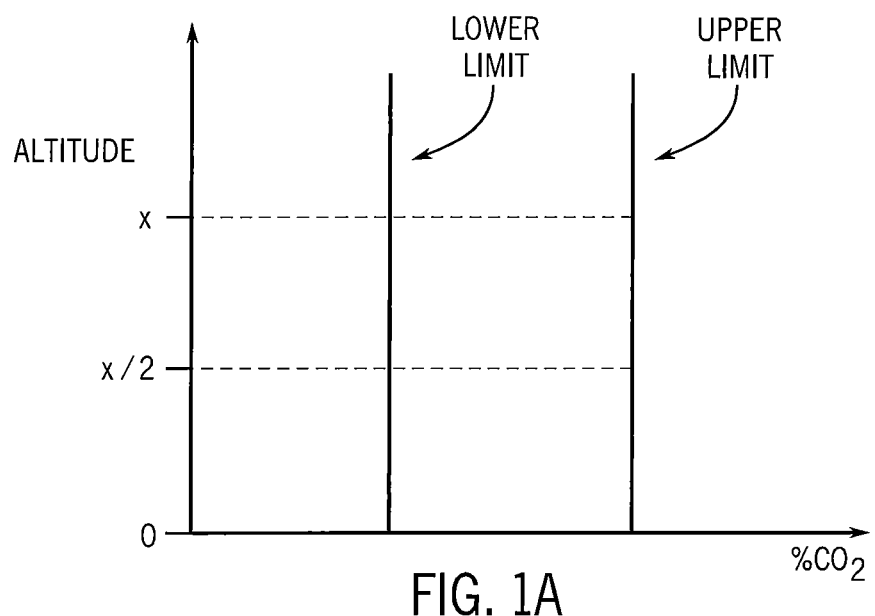
FIG. 1A is a graph illustrating a predefined lower limit value ('lower limit') and an upper limit value ('upper limit') of $CO_2$ concentration (percent $CO_2$) of an alarm for $CO_2$ related readings, the predefined lower and upper limits are constant in different altitudes such as at sea level (0), at x/2 meters above sea level, and at x meters above sea level.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

The present disclosure relates generally to the field of medical device alarms. There is provided, according to some embodiments, a method for updating alarm limits applied in monitoring one or more medical parameters of a patient, to comply with a detected ambient pressure.

There is provided, according to some embodiments, a method for updating alarm limits applied in monitoring one or more medical parameters of a patient, the method including measuring/obtaining a measurement of an ambient pressure at a defined time point ('$t_1$'); comparing the ambient pressure measured at the defined time point ('$t_1$') to a reference ambient pressure, and if a difference between the measured ambient pressure values at $t_1$ and the reference ambient pressure is at or above a predetermined threshold, updating the alarm limits to correspond with the ambient pressure at $t_1$ or alerting a user to update the alarm limits. Optionally, the reference ambient pressure is measured at a reference time point ('$t_0$'). Alternatively, the reference ambient pressure is a predetermined value. Ambient pressure may be measured using a pressure sensor. By way of non-limiting-example, the pressure sensor is a barometric sensor.

According to some embodiments, the method includes the steps of: measuring/obtaining a measurement of ambient conditions (such as, pressure and optionally also temperature) at a defined time point ('$t_1$'), comparing the ambient pressure measured at the defined time point ('$t_1$') to a reference ambient pressure measured at a reference time point ('$t_0$'), and if a difference between the measured ambient pressure values at $t_1$ and at $t_0$ is at or above a predetermined threshold, updating the alarm limits to correspond with the ambient pressure at $t_1$ or alerting a user to update the alarm limits. Optionally, in order to perform the update, the system will autozero (AZ) and calculate a constant (Z) that is utilized to multiply the alarm limits levels according to the autozero. According to some embodiments, the autozero may be a separate process initiated by an alarm module, not connected to a calibration process. According to some embodiments, the components/output readings of the $CO_2$ sensor assembly are affected by changes in ambient temperature and barometric pressure. As a result, the $CO_2$ measurement may no longer be accurate when the ambient conditions change. Thus, when the monitor detects that such ambient pressure and/or temperature changes, it triggers an autozero. Autozero may be automatic, not requiring a user interaction or programing of the monitor. According to some embodiments, the autozero stops the breath measurements and allows ambient air to enter the measurement chamber, e.g., through a secondary flow channel. This ambient air is then measured, and autozero reference is stored. The ambient air may be considered zero after a $CO_2$ scrubbing procedure.

For example, during patient monitoring, the medical device/system disclosed herein may measure an initial pressure when the medical device/system is turned on. In certain embodiments, an operator of the medical device/system may input the initial pressure. Once the initial pressure has been determined, the medical device/system may determine a first set of alarm limits. For example, the medical device/system may store predetermined alarm limits associated with various ambient pressures. In certain embodiments, the medical device/system may retrieve stored alarm limits from a database that stores predetermined alarm limits associated with a respective ambient pressure. In one embodiment, the medical device/system may store an algorithm that calculates the alarm limits based on the initial pressure (e.g., ambient pressure). When the patient is moved to another location having a different ambient pressure than the initial pressure, the medical device/system measures or retrieves from the database the ambient pressure at the other location. In certain embodiments, the operator of the medical device/system may input the ambient pressure at the location the patient has been moved to. The medical device/system may determine a second set of alarm limits based on the ambient pressure at the location the patient has been moved to. In this way, the medical device/system may update the alarm limits based on the ambient pressure at the location of the patient.

In one embodiment, the medical device/system may determine whether the change in ambient pressure is sufficient to change the alarm limits set using the initial ambient pressure, for example. For example, the medical device/system may determine a difference between the initial pressure (e.g., initial ambient pressure) and the pressure at the other location the patient has been moved (e.g., transferred) to. The pressure difference may be compared to a predetermined threshold value or range stored in the medical device/system. If the pressure difference is outside the predetermined threshold value or range, the medical device/system may update the alarm limits. If the pressure difference is within the predetermined threshold value or range, the medical device/system uses the alarm limits set using the initial pressure. In certain embodiments, the medical device/system may consider whether the change in ambient pressure is due to a change in altitude (e.g., if the patient is air lifted). If the pressure difference is due to a change in altitude, the medical device/system may update the alarm limits accordingly.

In one embodiment, after updating the alarm limits, a message is displayed on a display associated with the medical device to indicate that the alarm limits are updated (for example, "Alarm limits updating" or "Alarm updated").

In an embodiment, once the system determines that the alarm limits should be updated, a message appears on the display alerting the user that the alarm limits are being updated (for example, "Updating alarm limits").

In a further embodiment, the method is performed continuously during the monitoring of the one or more medical parameters. The method may be repeated in predefined time intervals during the monitoring of the one or more medical parameters.

In an embodiment, the alarm limits are updated to correspond to the ambient pressure at $t_1$ or the user is alerted to update the alarm limits, if a measured/computed altitude at $t_1$ is determined to be different than a reference altitude corresponding to the reference ambient pressure. The altitudes (e.g., the measured/computed altitude at $t_1$, and the reference altitude) may be determined by altimeters. By way of non-limiting example, the altimeters include barometric altimeters, radar altimeters, GPS based altimeters and other suitable sensors used to measure altitude. In a non-limiting example, the altitude is computed based on an ambient pressure measurement, for example, determined by a barometric sensor.

There is provided, according to some embodiments, a method for updating alarm limits applied in monitoring one or more medical parameters of a patient, the method including measuring a rate of change of ambient pressure during the monitoring of the one or more medical parameters, comparing the rate of change of ambient pressure to a predefined threshold, if the rate of change of ambient pressure is at or above the predefined threshold, updating the alarm limits or alerting a user to update the alarm limits.

According to some embodiments, the method includes measuring a rate of change of ambient pressure, comparing the rate of change of ambient pressure to a predefined threshold, if the rate of ambient pressure is at or above the predefined threshold, comparing a measured/computed altitude to a reference altitude, and if the measured/computed altitude deviates from the reference altitude, updating the alarm limits or alerting a user to update the alarm limits. The reference altitude may be measured/computed at a reference time point (e.g., initial time point) or alternatively the reference altitude may be predetermined.

According to some embodiments, there is provided an alarm limits update system including a control logic that may receive a measured rate of change of ambient pressure, compare the measured rate of change to a predetermined threshold value, and if the measured pressure rate is at or above the threshold value, update the alarm limits or alerting that such an update may be necessary. In certain embodiments, the control logic may compare a measured altitude to a reference altitude when the measured pressure rate is at or above the threshold value; and update alarm limits or alerting that such an update may be necessary, when the measured altitude deviates from the reference altitude.

According to some embodiments, there is provided an alarm limits update system including a control logic that may receive a measured rate of change of ambient pressure, compare the measured rate of change to a predetermined threshold value, compare a measured altitude to a predetermined initial altitude when the measured pressure rate crosses the threshold value, and update alarm limits or alerting that such an update may be necessary, when the measured altitude deviates from the predetermined initial altitude.

In one embodiment, the one or more medical parameters include a $CO_2$ related parameter, a respiration rate (RR), heart rate, an oxygen related parameter (e.g., $SpO_2$), spirometry, or any combination thereof. Each possibility is a separate embodiment. According to some embodiments, the $CO_2$ related parameter may include or may be derived from an expired/exhaled $CO_2$ related parameter. According to some embodiments, the $CO_2$ related parameter may include $EtCO_2$. Various $CO_2$ related parameters may be derived from the measurement of expired $CO_2$, such as, for example but not limited to: $CO_2$ waveform and parameters related thereto, respiration rate, breath cycle, $CO_2$ concentration in expired air, and the like, or any combination thereof. Each possibility is a separate embodiment.

Non-limiting examples of the $CO_2$ waveform related parameters include: $EtCO_2$, changes in $EtCO_2$, a slope of an increase in the $CO_2$ concentration, a change in a slope of the increase in the $CO_2$ concentration, a time to rise to a predetermined percentage of a maximum value of $CO_2$ concentration, a change in the time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, a breath to breath correlation, a change in breath to breath correlation, a $CO_2$ duty cycle, a change in $CO_2$ duty cycle, a minute ventilation, a change in minute ventilation, or any combination thereof.

According to some embodiments, the term "end tidal $CO_2$" ($EtCO_2$) refers to the partial pressure or maximal concentration of carbon dioxide ($CO_2$) at the end of an exhaled breath, which may be expressed, for example, as a percentage of $CO_2$ or mmHg. $EtCO_2$ is an approximate estimation of the alveolar $CO_2$ pressure and thus of the arterial levels of $CO_2$. The normal values of $EtCO_2$ as measured at ambient pressure may vary depending on the ambient conditions (e.g., pressure) and may be in the range of approximately 29-45 mmHg (for example, 30-35, 33-37, 34-35 mmHg). $EtCO_2$ may rise above the normal range, such as, in cases of respiratory distress. For example, during respiratory distress, increased effort to breathe does not effectively eliminate $CO_2$. This may lead to $CO_2$ accumulation in the lungs and excreted with each breath (hypercapnea). $EtCO_2$ reading may be below the normal range, such as, in cases of pulmonary embolism. During a pulmonary embolism, a blocked pulmonary artery causes less $CO_2$-rich blood to return to the lungs and consequently less $CO_2$ is released with each breath.

As referred to herein, the terms "patient" and "subject" may interchangeably be used and may relate to a subject being monitored by any monitoring device for any physical-condition related parameter and/or health related parameter.

As used herein, the terms "alarm" and "traditional alarm" may interchangeably refer to an alarm that may be triggered when a medical parameter crosses a predetermined alarm threshold. According to some embodiments, the alarm threshold may be a range, a range that may be a function of time for which the alarm state has been reached, a range that may be a function of by how much the threshold has been passed or any combination thereof. Each possibility is a separate embodiment.

Figure 1B:
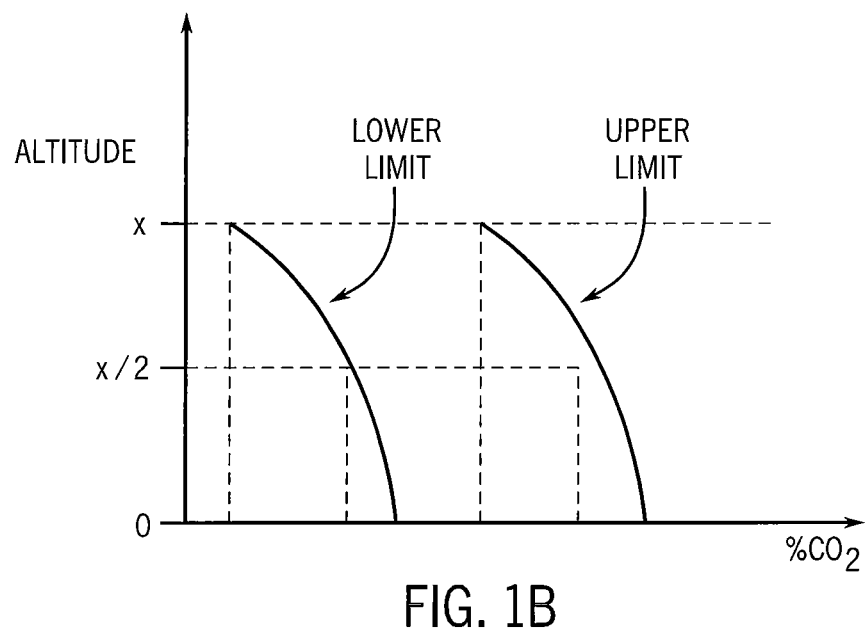
FIG. 1B is a graph showing a predefined lower limit value ('lower limit') and an upper limit value ('upper limit') of $CO_2$ concentration (percent $CO_2$) of an alarm for $CO_2$ related readings, which are updated to comply with the effect of ambient pressure at different measured altitudes such as at sea level (0), at x/2 meters above sea level, and at x meters above sea level.

As referred to herein, the term "ambient pressure" refers to the pressure of the surrounding atmosphere. As discussed above, ambient pressure changes with altitude. For example, ambient pressure at sea level is 101.3 kiloPascals (kPa) or 1 atmosphere, at 900 meters above sea level the ambient pressure is 90.9 kPa, and at 2700 meters above sea level it is 72.8 kPa. Therefore, parameters such as $CO_2$ readings, which are affected by ambient pressure, change with altitude. As demonstrated in the graph of FIG. 1A, in cases in which the alarm limits are constant predefined limits, the alarm limits remain constant when altitude changes. Alarm limits, of the devices and method disclosed herein, according to some embodiments, are updated (for example, periodically or constantly) to comply with the change of ambient pressure as a function of altitude, as demonstrated in the graph of FIG. 1B. In such case, the lower limit and the upper limit decrease when the altitude increases from 0 to X/2 and further decrease when the altitude increases from X/2 to X. It is noted that FIG. 1B is merely a schematic representation and the graph representing the change of alarm limits (lower/upper) in different altitudes may have other shapes or forms. According to some embodiments, the change of lower alarm limits and the change of upper alarm limits with altitude may be the same or different.

Figure 2:
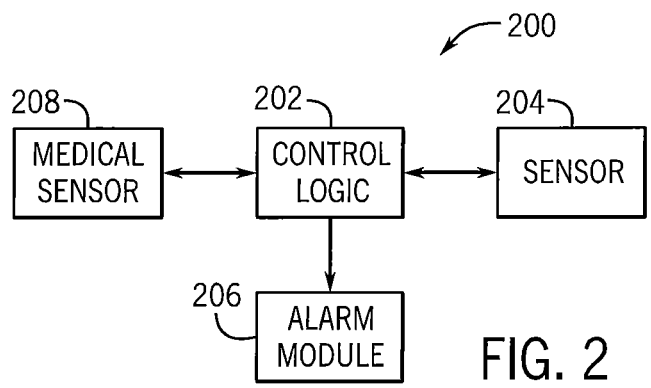
FIG. 2 schematically illustrates a medical device with a control logic, according to some embodiments.

Reference is now made to FIG. 2, which illustrates a medical device/system 200 with a control logic 202 that may be used for updating alarm limits applied in monitoring of one or more medical parameters (such as a $CO_2$ related parameter or any other medical parameters, which may be affected by changes in ambient pressure), in accordance with some embodiments. Control logic 202 of medical system 200 may receive measured ambient pressure values from an ambient pressure sensor 204, to compute a change or a rate of change in ambient pressure, to compare the computed change or the computed rate of change to a predefined threshold, and to update alarm limits (e.g., $CO_2$ alarm limits) of an alarm module 206, if the computed change or the computed rate of change is at or above the predefined threshold.

The ambient pressure sensor 204 may be embedded in control logic 202. Alternatively, ambient pressure sensor 204 may be located away from control logic 202, such as part of another device or system that communicates its ambient reading to control logic 202 or to a third-party processor. In certain embodiments, the medical device/system 200 may include a secondary flow channel in a measurement chamber that receives ambient air. A pressure of the ambient air in the secondary flow channel is measured to determine a reference ambient pressure. The reference ambient pressure may be stored in the computer logic 202 and used to autozero the medical device/system 200. Alarm limits may be determined based on the ambient pressure.

System 200 further includes a medical sensor 208, such as a $CO_2$ sensor (assembly) that may measure $CO_2$ in expired breath of a subject, or any other sensor measuring a medical parameter, which may be affected by changes in ambient pressure.

Figure 3:
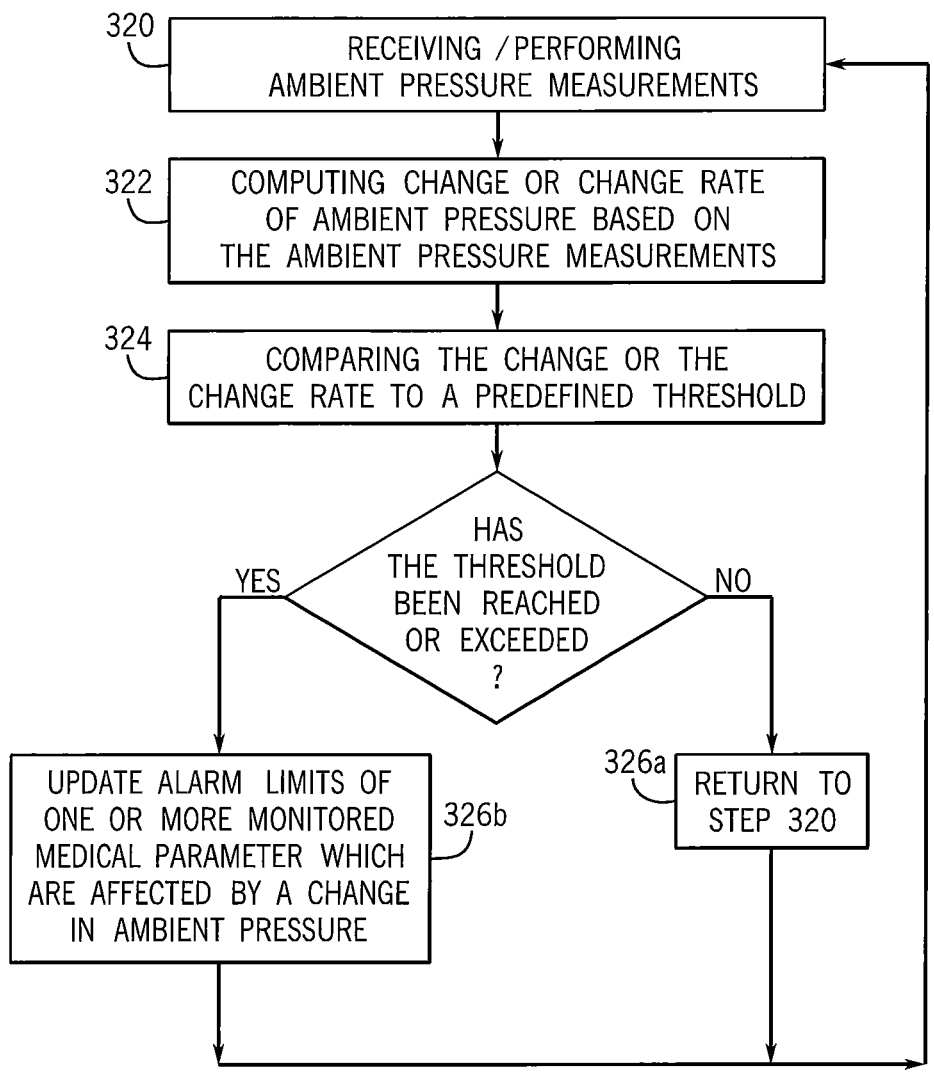
FIG. 3 is an illustrative flowchart of a method for updating alarm limits to comply with a detected ambient pressure, according to some embodiments.

Reference is now made to FIG. 3, which is a flowchart of a method for updating alarm limits applied in monitoring one or more medical parameters which are affected by a change in ambient pressure, in accordance with some embodiments.

Ambient pressure measurements are received/performed (step 320). In certain embodiments, the ambient pressure measurements are received from a dedicated sensor, such as a barometric pressure sensor. The measurement may be performed continuously or repetitively in constant time intervals during a monitoring of the one or more medical parameters.

Change or rate of change in ambient pressure is determined based on the one or more ambient pressure measurements (step 322). The change in ambient pressure may be determined based on a comparison of ambient pressure measured at a defined time point ('$t_1$') to a predefined reference ambient pressure, or to an ambient pressure measured at a reference time point ('$t_0$'), such as an initial time point. The rate of change of ambient pressure may be determined based on several ambient pressure measurements during a predefined time duration.

The rate of change or the change in ambient pressure is compared to a predefined threshold value (step 324). If the threshold value is not reached or exceeded, no action is triggered and the control logic may return to step 320 (step 326a). However, if the threshold value is reached or exceeded, the control logic updates alarm limits of an alarm applied in monitoring one or more medical parameters, which are affected by change in ambient pressure or alerts a user that an update of the alarm limits may be necessary (step 326b).

In one embodiment, the method is continuously repeated or repeated in predefined time intervals during the monitoring of the one or more medical parameters. The method may be repeated in response to an input from an operator.

Figure 4:
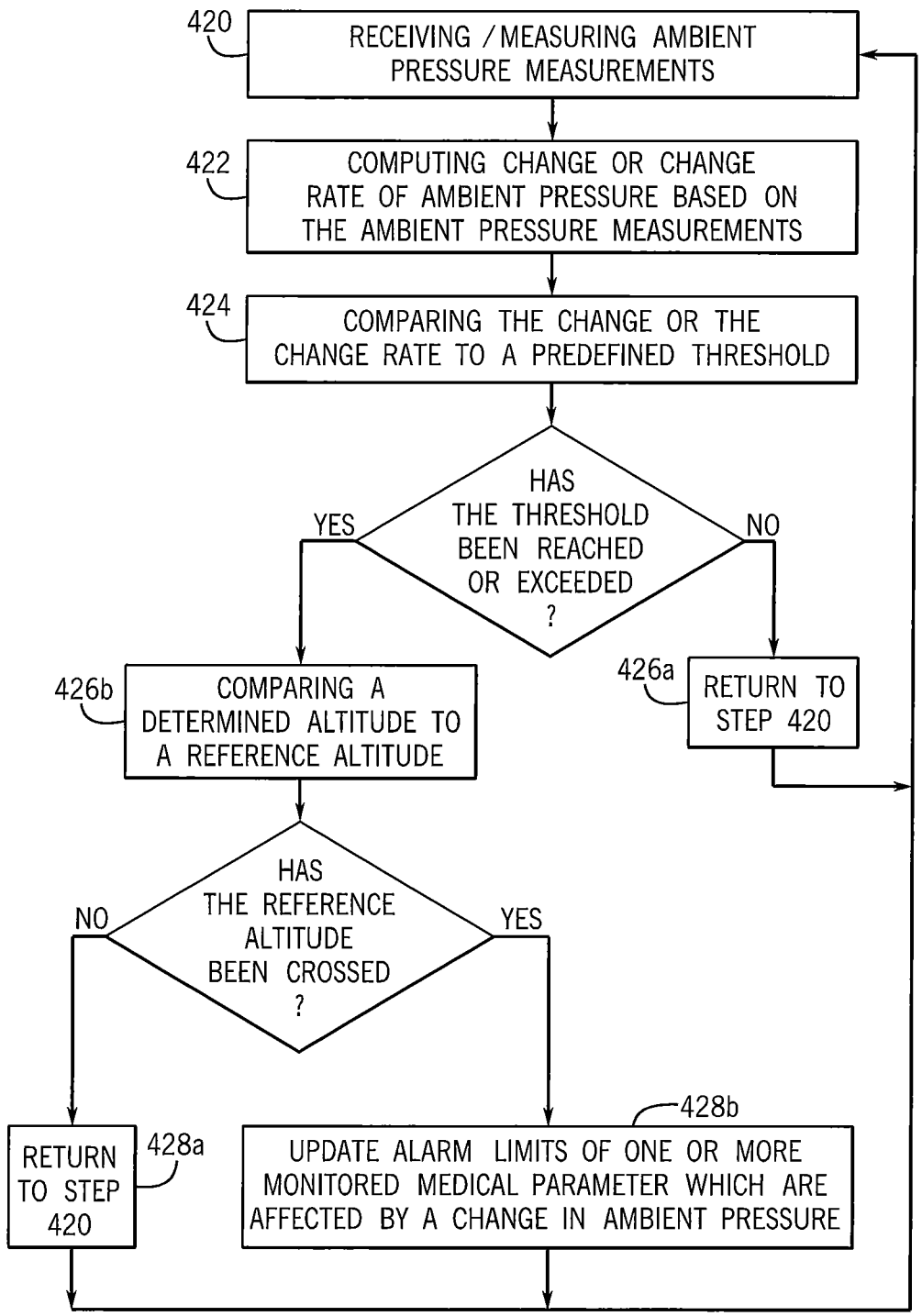
FIG. 4 is an illustrative flowchart of a method for updating alarm limits to comply with a detected ambient pressure, according to some embodiments.

Reference is now made to FIG. 4 which is a flowchart of a method for updating alarm limits applied in monitoring one or more medical parameters affected by a change in ambient pressure, in accordance with some embodiments.

Ambient pressure measurements are received/obtained (step 420). In certain embodiments, the one or more ambient pressure measurements are received from a dedicated sensor, such as a barometric pressure sensor. The measurement may be performed continuously or repetitively in constant time intervals during a monitoring of the one or more medical parameters.

Change or rate of change of ambient pressure is determined based on the ambient pressure measurements (step 422). The change in ambient pressure may be determined based on a comparison of ambient pressure measured at a defined time point ('$t_1$') to a predefined reference ambient pressure, or to an ambient pressure measured at a reference time point ('$t_0$'), such as an initial time point, or measured at a previous operation cycle of the disclosed method. The rate of change in ambient pressure may be determined based on several ambient pressure measurements during a predefined time duration.

The rate of change or the change in ambient pressure is compared to a predefined threshold value (step 424). If the threshold value has not been reached or exceeded, no action is triggered and the control logic may return to step 420 (step 426a). However, if the threshold value has been reached or exceeded, a determined/computed/measured altitude is compared to a reference altitude (step 426b). The reference altitude may be predefined, or alternatively measured at a reference time point such as an initial time point, or at a previous operation cycle of the disclosed method.

If the reference altitude has not been crossed, no action is triggered and the control logic may return to step 420 (step 428a). If the reference altitude has been crossed (i.e. the detected altitude is lower or higher than the reference altitude), the control logic updates alarm limits of an alarm applied in monitoring one or more medical parameters, which are affected by a change in ambient pressure or alerts a user that the alarm limits should be changed (step 428b).

In one embodiment, the method is continuously repeated or repeated in predefined time intervals during the monitoring of the one or more medical parameters. The method may be repeated in response to input from an operator.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. Unless otherwise defined, all technical and scientific terms used herein have the same meaning as commonly understood by one of ordinary skill in the art to which this disclosure belongs.

Unless specifically stated otherwise, as apparent from the following discussions, it is appreciated that throughout the specification discussions utilizing terms such as "processing", "computing", "calculating", "determining", "estimating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

The present disclosure may be a system, a method, and/or a computer program product. The computer program product may include a computer readable storage medium (or media) having computer readable program instructions thereon for causing a processor to carry out aspects of the present disclosure.

Embodiments of the present disclosure may include apparatuses for performing the operations herein. This apparatus may be specially constructed for the desired purposes, or it may include a general purpose computer selectively activated or reconfigured by a computer program stored in the computer. Such a computer program may be stored in a computer readable storage medium, such as, but not limited to, any type of disk including floppy disks, optical disks, CD-ROMs, magnetic-optical disks, read-only memories (ROMs), random access memories (RAMs), electrically programmable read-only memories (EPROMs), electrically erasable and programmable read only memories (EE- PROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present disclosure are not described with reference to any particular programming language. It will be appreciated that a variety of programming languages may be used to implement the teachings of the disclosures as described herein.

The disclosure may be described in the general context of computer-executable instructions, such as program modules, being executed by a computer. Generally, program modules include routines, programs, objects, components, data structures, and so forth, which perform particular tasks or implement particular abstract data types. The disclosure may also be practiced in distributed computing environments where tasks are performed by remote processing devices that are linked through a communications network. In a distributed computing environment, program modules may be located in both local and remote computer storage media including memory storage devices.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

What is claimed is:

1. A method for updating alarm limits applied in monitoring one or more medical parameters of a subject, the method comprising:
   obtaining a measurement of ambient pressure at a defined time point ('$t_1$');
   automatically comparing the measurement of ambient pressure to a reference ambient pressure; and
   updating the alarm limits to correspond with the ambient pressure at $t_1$ or alerting a user to update the alarm limits in response to a difference between the measured ambient pressure at $t_1$ and the reference ambient pressure being at or above a predetermined threshold, wherein the alarm limits include lower and upper alarm limit values and are applied in monitoring one or more medical parameters of a subject, and wherein the one or more medical parameters are affected by a change in ambient pressure.

2. The method of claim 1, further comprising the step of measuring the ambient pressure at the defined time point ('$t_1$').

3. The method of claim 1, wherein the reference arrtbient pressure is measured at a first time point ('$t_0$').

4. The method of claim 1, wherein the reference ambient pressure is a predetermined value.

5. The method of claim 1, wherein the one or more medical parameters comprises a $CO_2$ related parameter.

6. The method of claim 5, wherein the $CO_2$ related parameter is selected from the group consisting of: $EtCO_2$, $CO_2$ waveform and, parameters related thereto, respiration rate, breath cycle, $CO_2$ concentration in expired air and any combination thereof.

7. The method of claim 1, wherein the $CO_2$ related parameter comprises $EtCO_2$.

8. A method for updating alarm limits applied in monitoring one or more medical parameters of a subject, the method comprising:
   obtaining a measurement of a rate of change of ambient pressure during the monitoring of the one or more medical parameters;
   comparing the rate of change of ambient pressure to a predefined threshold; and
   updating the alarm limits or alerting a user to update the alarm limits in response to the rate of change of ambient pressure being at or above the predefined threshold.

9. The method of claim 8, comprising measuring the rate of change of ambient pressure.

10. The method of claim 8, wherein the one or more medical parameters comprises a $CO_2$ related parameter.

11. The method of claim 10, wherein the $CO_2$ related parameter is selected from the group consisting of: $EtCO_2$, $CO_2$ waveform, and parameters related thereto, respiration rate, breath cycle, $CO_2$ concentration in expired air and any combination thereof.

12. The method of claim 8, wherein the $CO_2$ related parameter comprises $EtCO_2$.

13. A device for updating alarm limits applied in monitoring one or more medical parameters of a subject, the device comprising a medical device comprising a processor configured to:
   receive a signal indicative of a change and/or a rate of change of ambient pressure;
   compare the change and/or the rate of change to one or more predetermined threshold values, and
   update the alarm limits or alert a user to update the alarm limits in response to the change and/or the rate of change of ambient pressure is at or above the one or more predetermined threshold values, wherein the alarm limits are applied in monitoring one or more medical parameters of the subject, and wherein the one or more medical parameters vary with ambient pressure.

14. The device of claim 13, wherein the one or more medical parameters comprises a $CO_2$ related parameter.

15. The device of claim 14, wherein the $CO_2$ related parameter is selected from the group consisting of: $EtCO_2$, $CO_2$ waveform, and parameters related thereto, respiration rate, breath cycle, $CO_2$ concentration in expired air, and any combination thereof.

16. A system for updating alarm limits applied in monitoring one or more medical parameters of a subject, the system comprising:
   medical device including a processor configured to:
      receive a signal indicative of a change and/or a rate of change of ambient pressure;
      compare the change and/or the rate of change to one or more predetermined threshold values; and
      update the alarm limits or alert a user to update the alarm limits when the change and/or the rate of change of ambient pressure is at or above the one or more predetermined threshold values, wherein the alarm limits include lower and upper alarm limit values and are applied in monitoring one or more medical parameters of a subject; and
   a sensor configured to measure the one or more medical parameters, wherein the one or more medical parameters vary with ambient pressure.

17. The system of claim 16, further comprising a pressure sensor configured to measure ambient pressure values and to communicate the measured ambient pressure values to the processor.

18. The system of claim 16, wherein the one or more medical parameters comprises a $CO_2$ related parameter.

19. The system of claim 18, wherein the $CO_2$ related parameter is selected from the group consisting of: $EtCO_2$, $CO_2$ waveform, and parameters related thereto, respiration rate, breath cycle, $CO_2$ concentration in expired air, and any combination thereof.

20. The system of claim 18, wherein the $CO_2$ related parameter comprises $EtCO_2$.

* * * * *